United States Patent [19]

Eyal et al.

[11] Patent Number: 5,137,826
[45] Date of Patent: Aug. 11, 1992

[54] *MORCHELLA ROTUNDA* SP. USEFUL FOR PRODUCING NATURAL BLUE PIGMENT

[75] Inventors: Jacob Eyal, Baltimore; Michael G. Spencer, Ellicott City, both of Md.

[73] Assignee: W. R. Grace & Co.-Conn., New York, N.Y.

[21] Appl. No.: 719,435

[22] Filed: Jun. 24, 1991

Related U.S. Application Data

[62] Division of Ser. No. 494,243, Mar. 15, 1990.

[51] Int. Cl.⁵ .................. C12N 1/14; C12R 1/645
[52] U.S. Cl. ................... 435/254; 435/119; 435/911; 47/1.1
[58] Field of Search .............. 435/119, 911, 254; 47/1.1

[56] References Cited

U.S. PATENT DOCUMENTS

| | | | |
|---|---|---|---|
| 4,442,209 | 4/1984 | Miyake et al. | 435/119 |
| 4,520,103 | 5/1985 | Ensley | 435/121 |
| 4,594,809 | 6/1986 | Ower et al. | 47/1.1 |
| 5,077,201 | 12/1991 | Eyal et al. | 435/254 |

OTHER PUBLICATIONS

"Catalogue of ATCC Fungi/Yeasts", 17th Ed. 1987 Editor Jong et al., p. 219.

*Primary Examiner*—Herbert J. Lilling
*Attorney, Agent, or Firm*—Jill H. Krafte

[57] ABSTRACT

A novel mutant strain of Morel mushroom has been found to produce the blue pigment indigo by submerged nutrient culture medium containing a carbon and a fermentation in a nitrogen substrate. A red/purple pigment is also produced. The novel strain is *Morchella rotunda* nov. ES-1 sp. ATCC 20951.

5 Claims, No Drawings

MORCHELLA ROTUNDA SP. USEFUL FOR PRODUCING NATURAL BLUE PIGMENT

This is a division, of application Ser. No. 494,243, filed Mar. 15, 1990.

BACKGROUND OF THE INVENTION

This invention relates to a process for producing a natural blue pigment by submerged fermentation of a mutant Morel mushroom fungus, Morchella nov. ES-1 sp. This vivid blue pigment is useful in food, drug, medical device, cosmetic and textile coloring or dying applications. The pigment has been identified as indigo (or indigotin, as it is also called).

The use of synthetic pigments in cosmetic, food and medical applications is increasingly questioned for safety reasons. Various synthetic coloring agents have been banned as edible coloring agents due to potential carcinogenicity or teratogenicity. In addition, publicity and consumer education on this topic has led to increasing interest in and demands for the use of safer, naturally occurring pigments and coloring agents.

Indigo is a naturally occurring glucoside found in many plants, particularly of the genera Indioofera and Isatus. Indigo released from such plants has been used as a textile dye for thousands of years.

Naturally occurring pigments typically have certain limitations, however. They may be of lower tinctorial strength than synthetic colorants. In addition, the pH of various food and cosmetic products is known to affect the shade of the pigment, as well as its stability to heat, light and preservatives.

The production of indigo by submerged culture of bacterial strains (e.g., *Pseudomonas indoloxidans, Mycobacterium qloberulum, Micrococcus piltonensis*) isolated from soil samples using indole as a source of carbon and nitrogen in the medium has been reported by Gray, "Formation of Indigotin from Indole by Soil Bacteria," Roy. Soc. Proc., 102:263-80(1972).

U.S. 4,520,103 (Ensley, Jr.) reported microbiological production of indigo in a genetically-transformed microorganism grown in an indole-free medium. The microorganism used was selected on the basis of having the metabolic capacity to produce and accumulate indole. The genetic transformation incorporated the capacity to synthesize one or more aromatic dioxygenase enzymes which catalyze the oxidative transformation of the accumulated indole. The reaction product is further processed by the cell to indigo.

Miles et al., "The Identification of Indigo as a Pigment Produced by a Mutant Culture of *Schizophyllum commune*," Arch. Biochem. and Biophys., 62:1-5(1956), identified as indigo a blue pigment harvested from mycelial macerates of a mutant culture of *Schizophyllum commune* fungus. Falanghe et al., "Identification of Indigo Produced in Submerged Culture of *Acaricus camoestris*, Mutant Culture," Arch. of Biochem. and Biophys., 96:430-33(1962), isolated a single mutant strain of *Agaricus campestris* which produced a blue color in the medium. The blue coloring matter was isolated and separated into three main fractions, one of which was identified as indigo.

SUMMARY OF THE INVENTION

The present invention provides a naturally occurring blue pigment or coloring agent, which has been identified as indigo (or indigotin). A method is disclosed for production of the blue pigment using submerged fermentation of a mutant mushroom mycelium. The invention comprises the blue pigment and the mutant species of Morel mushroom, Morchella nov. ES-1 sp., which has been found to produce the pigment. The invention further comprises a method for producing and extracting the blue pigment from the mutant mushroom mycelium.

It is the primary purpose of this invention to provide a naturally occurring blue pigment or coloring agent which can be suitable for use in foods, drugs, medical devices, cosmetics and textiles.

A closely related purpose is to provide a coloring agent which is safe and non-toxic for such uses.

A further related object is to provide a stable blue pigment or coloring agent, whose tinctorial strength is not diminished by exposure to a variety of temperatures or pHs.

It is also an object to provide a novel fungal source for the blue pigment indigo, as well as a process for obtaining indigo in q:antities and purity suitable for use in foods, drugs, cosmetics and textiles. It is particularly desired to provide a means for preparing indigo in the complete absence of exogenous indole. It is also desired to prepare indigo in submerged culture.

DETAILED DESCRIPTION OF THE INVENTION

It has been found that a novel mutant Ascomycetes (mushroom) fungus is capable of producing a dark blue pigment by employing submerged fermentation culture of the mushroom mycelium. A blue pigment is spontaneously produced and accumulated intracellularly in the fungal mycelia as well as extracellularly in the fermentation medium. The pigment may be separated from the medium or may be extracted from the mycelium, and may be crystallized. This pigment has been identified as indigo.

A novel mutant strain of Morchella fungus has been obtained by treating the fungus *Morchella rotunda* ATCC 14071 with the antibiotic chloramphenicol. This parent strain is an edible mushroom strain of the type commonly known as Morel mushroom. The mutant strain, designated Morchella nov. ES-1 sp., has been deposited with the American Type Culture Collection ("ATCC"), 12301 Parklawn Drive, Rockville, Md., U.S.A., and has been given accession number ATCC 20951. Blue pigment, identified as indigo, is produced and accumulated during submerged fermentation of the mycelia of the mutant mushroom strain. The mycelium is the vegetative portion of a fungus composed of a network of filaments called hyphae.

When grown on agar, the mutant fungus develops fuzzy white aerial hyphae, with some diffusion of blue pigment from hyphae growing below the surface of the solid agar medium. In submerged culture fermentation, or for fungal growth occurring beneath the surface of a solid agar culture, a vivid blue pigment is produced in the mycelium. Upon microscopic examination, this pigment was determined to be produced intracellularly, in the wall of the hyphal mycelium, in the form of small granules. The pigment is accumulated in the hyphae, with some pigment found extracellularly in the medium as well.

The mushroom mycelia may conveniently be pre-grown on solid agar media. The Morchella nov. ES-1 sp. strain conveniently may be maintained on a solid agar medium composed of glucose (1.5%), peptone (0.3–0.5%), yeast extract (0.3–0.5%), malt extract (0.3–0.5%) and agar (1.5–2.0%). Somewhat varied concentrations or other standard or specialized media with sufficient nutrients to support and maintain strain viability may be used, if desired.

After sufficient pre-growth (e.g., preferably about 2–5 days), the mycelia are removed from the agar and transferred to the culture broth. Preferably, the mycelia are homogenized prior to transfer. To begin the submerged culture fermentation, the mutant mushroom mycelia are grown in a liquid nutrient containing sufficient nutrients to meet the needs of the Morchella nov. ES-1 sp. fungus, that is, a culture broth containing one or more assimilable carbon and nitrogen sources, as well as inorganic salts and, where desired, other minor organic nutrients.

All customary carbon sources can be used. Preferred carbon sources for this mutant strain include glucose, maltose and cane sugar. Xylose, sugar alcohols such as mannitol or glycerol, and naturally occurring mixtures such as malt extract, molasses or whey can be used. Any convenient organic and inorganic nitrogen source may be used. For example, amino acids, protein hydrolysates, nucleosides, soybean meal, cottonseed meal, pea meal, soluble and insoluble vegetable proteins, yeast extract, peptone and meat extracts may be used, as well as ammonium salts and nitrates such as urea, $NH_4Cl$, $(NH_4)_2SO_4$, $NH_4NO_3$ and $KNO_3$ will be suitable.

Inorganic elements (minerals) (e.g., potassium phosphate, magnesium sulfate) and/or vitamins (e.g., biotin, thiamine) should be added as well. Mineral salts which should be present in the medium are supplied by the following ions: $Mg^{++}$, $Ca^{++}$, $NH_4^{++}$, $K^-$, $Cl^-$, $SO_4^{-2}$, $PO_4^{3}$. Ions of the usual trace elements also should be present: Cu, Fe, Mn, Mo and Zn. Where complex carbon and/or nitrogen sources are present which provide these salts and trace minerals, the mutant strain grows well and produces pigment in the absence of specifically added minerals.

In general, the medium preferably should contain about 0.5 to 20.0%, most preferably about 2.0–5.0%, of a carbon substrate. Preferably the nitrogen substrate will be about 30 to 50% of the carbon substrate, or about 0.5 to 5.0%, most preferably about 1.33% of the medium. Mineral salts should be present in quantities from about 0.1 to 2.0%, preferably about 0.5%. Trace elements and vitamins should be included in concentrations from about 2.0 to about 50.0 ppm, preferably about 25.0 ppm. This medium may be adjusted somewhat, but decreasing or omitting the minerals and trace elements, or making significant adjustments to other components of the medium, may result in reduction of indigo produced. Thus, use of the medium as described here will serve to maximize indigo production.

Submerged fermentation may be conducted in shake flasks or in larger scale fermentation equipment. Conventional fermentation temperatures between about 20° C. and about 35° C. may be used, preferably temperatures below about 25°–30° C. The pH preferably should be maintained at about 4.5 to 6.5, most preferably 4.5 to 5.5, for maximum indigo production.

The pigment is spontaneously produced in the submerged mushroom mycelium as a secondary metabolite. In the first phase of metabolism, glucose (or another carbohydrate source) is exhausted and the mycelial pellet produced. Upon exhaustion of the carbohydrate source, Morchella nov. ES-1 sp. (ATCC 20951) spontaneously begins to produce and accumulate granules of blue pigment. No further induction is required and no inducing compounds are necessary. The pigment generally tends to remain associated with the cell wall, although autolysis of the mycelium releases some pigment into the medium, where it is slightly soluble. This release of pigment turns the medium first blue, then navy blue/black in color. The majority of the pigment will be recoverable from the mycelium, and remaining pigment may be extracted from the medium as well.

As mentioned, blue pigment begins to accumulate as the carbohydrate source in the fermentor is exhausted. For example, in the shake flask experiments described in the Examples, particles or small granules of blue pigment began to appear intracellularly in the mycelia after about 36 hours. The pigment appears microscopically as a continuous granulated layer inside the hyphae of some filaments. In other filaments, large granules of pigment are seen outside the mycelium. Continued fermentation with additional carbohydrate added (i.e., fed-batch fermentation) preferably is continued in order to maximize pigment production. In such fed-batch fermentaton, it is advantageous to begin cultivation using a very low concentration of nutrients, i.e., 2.0–3.0% carbon substrate and 0.8–1.3% nitrogen substrate. As blue pigment development occurs, the fermentation vessel may be fed with additions of concentrated, sterile nutrient medium at a rate which maintains the glucose (or other carbon substrate) level at about 0.05–0.2%, in order to maximize blue pigment production.

The mycelia are removed from the medium at the desired time or stage by filtration, centrifugation or other convenient separation means. It is preferred to dry the mycelia prior to extracting the blue pigment, in order to improve the purity and yield of the extraction. Vacuum drying, air drying or oven drying may be employed. Temperatures preferably are elevated to about 30°–50° C. In order to prevent the indigo from being damaged, it is recommended that temperatures be kept below about 100° C., most preferably below about 90° C. Preferably, the dried mycelia are ground, cut or homogenized into small particles in order to facilitate extraction. The dried mycelium particles are then mixed with an extractant. Alternatively, the mycelia, either dried, partially dried or as separated from the fermentation medium, may be mixed with the extractant and then cut up and agitated, i.e., in a blender or homogenizer. In yet another alternative, the wet mycelia may be homogenized and then mixed with the extractant. In either alternative, the mycelia are agitated with the extractant, preferably for about 24 hours.

Extraction with chloroform, ether or ethyl acetate yields a dark blue solution which is very stable. This blue solution can easily be concentrated and dried. Non-toxic solvents, such as aqueous sulfuric acid, may be used for food or drug applications of the pigment. Extraction with solvents such as acetone, hexane or benzene result in partial dissolution of the blue pigment yielding purple solutions with reddish tints, but these solvents are less preferred where complete extraction is desired. The mycelia may be put through multiple extractions to remove additional pigment. The blue pigment is slightly soluble in water, ethanol and methanol and in aqueous sulfuric acid.

The mycelia and extractant are thoroughly mixed and then separated using conventional methods (e.g., centrifugation, filtration), with the blue pigment now dissolved in the extractant. If a non-toxic solvent is used as the extractant, the blue solution may be used directly as a coloring agent. Or, the solution may be concentrated and dried. This will be particularly important where the extractant is a toxic solvent. Vacuum drying evaporation is particularly suitable. Alternatively, the blue solution can be concentrated to form a dark blue suspension. Upon cooling to about 4° C., blue crystals precipitate and can be collected.

The blue solution obtained by this process also comprises a red/purple component produced by the mutant mycelium. The colored solution can be used at this point, or the blue pigment may be further purified by separating it from the red/purple pigment. This can be done by adsorption with alumina or silica gel. The red/purple pigment is preferentially soluble in acetone. Eluting the pigment product from the alumina or silica gel several times with acetone will therefore yield an insoluble fraction of blue pigment.

The blue pigment can be crystallized, as described above, forming cubic crystals. The pigment is color-stable under widely varying conditions. It has been shown to be stable on exposure to pH from 2 to 12. The significance of this characteristic is that the pigment will be useful as a food coloring agent without breakdown at the pH levels of various foods. The pigment also is stable to high temperatures of up to at least about 300° C. without breakdown or loss of color, and is stable on exposure to light. The pigment has been identified as indigo, based on absorption spectrum and mass spectrum analyses. The absorption spectrum of pigmented culture filtrate from growth of ATCC 20951 is characterized by two absorption peaks at 285 and 604 nm, which indicates that the pigment is indigo (or indigotin, as it is also called).

As described above, chloroform, ether, sulfuric acid and ethyl acetate are excellent solvents for the pigment. Alternatively, the pigment may be used in dried form, or may be emulsified or put on a suitable carrier. The presence of water or hydrocarbons, including carbohydrates, do not affect the stability or color of the pigment.

The examples which follow are given for illustrative purposes and are not meant to limit the invention described herein. The following abbreviations have been used throughout in describing the invention. All percentages are weight/volume percents, unless otherwise indicated.

° C.—degrees Centigrade
gm—gram(s)
L—liter(s)
mg—milligram(s)
ml—milliliter(s)
μm—micrometer(s)
nm—nanometer(s)
%—percent
ppm—part(s) per million
rpm—revolutions per minute
vvm—volume of air sparging through volume of medium per minute

EXAMPLE I

Morchella nov. ES-1 sp. (ATCC 20951) mycelia were maintained on solid agar slant tubes (1.5% glucose, 0.5% peptone, 0.5% yeast extract, 0.5% malt extract and 1.5% agar) at 4° C. The mycelia were inoculated onto fresh slant tubes and incubated for 5 days at 30° C. The agar medium and mycelia were homogenized using a Tekmar Tissumizer ™ homogenizer (Tekmar Company) and transferred to a 500 ml shake flask containing 300 ml of the following medium:

| | |
|---|---|
| 30.0 | gm/L Glucose, |
| 1.0 | gm/L MgSO$_4$.7H$_2$O, |
| 5.0 | gm/L Casamino acid, |
| 5.0 | gm/L Yeast extract, |
| 5.0 | gm/L Soytone, |
| 6.7 | gm/L NH$_4$NO$_3$, |
| 1.0 | gm/L KH$_2$PO$_4$, |
| 0.1 | gm/L CaCl$_2$.2H$_2$O, |
| 0.025 | gm/L CuSO$_4$, |
| 0.054 | gm/L FeCl$_3$.6H$_2$O, |
| 0.085 | gm/L MnSO$_4$.4H$_2$O, |
| 0.24 | gm/L Na$_2$MoO$_4$.2H$_2$O, |
| 0.144 | gm/L ZnSO$_4$.6H$_2$O, |
| 0.02 | gm/L Thiamine HCl. |

The shake flasks were incubated for three days at 150 rpm at 28° C. The mycelia produced by the end of three days were in the form of beads with an average size of about 5-10 mm and were white in color, with flecks of dark blue interspersed throughout the mycelial bead. A band of intense blue color appeared at the surface of the medium. The medium had changed from yellow to dark blue.

For each flask, the resulting mycelia, which exhibited intracellular blue granules, were filtered, homogenized and re-suspended in 300.0 ml ethyl acetate. The supernatant (i.e., the culture medium) was separately extracted (1:1) with 300.0 ml ethyl acetate. The extracts were pooled and evaporated under vacuum at 35° C. to yield 50.0 ml dark blue concentrated liquid.

The blue concentrate was loaded onto a silica gel column (200 μm particle size chromatographic grade silica gel (Amicon Div., W. R. Grace & Co.-Conn.)) using a mobile phase of 50% ethyl acetate and 50% hexane. Four different fractions appeared: blue, red, yellow and green. The blue and red fractions were collected and evaporated under vacuum to yield 20 ml volumes of concentrated dark blue and red fractions, respectively. The suspension was cooled to 4° C. and blue crystals precipitated out. The isolated blue crystals were stable at pHs in the range 2-12. Upon microscopic examination, the pigmented crystals were found to be cubic in shape. Mass spectroscopy confirmed that the pigment was indigo.

The red fraction was highly unstable, particularly on exposure to light, where it turned brownish and then yellowish. The pigment in this fraction was identified by absorption analysis as indirubin, a position isomer of indigo.

EXAMPLE II

Morchella nov. ES-1 sp. (ATCC 20951) were grown and cultivated by submerged fermentation as in Example I. The resulting mycelia were filtered from the fermentation medium and dried under vacuum overnight at 35° C. The dried mycelia were ground and placed in 500 ml chloroform with the filter paper holding the dried mycelia, agitated overnight and refiltered. The filtrate was evaporated until dry. The dried residue was washed several times with acetone to remove red/purple pigment. The purified blue pigment was vacuum dried, forming blue crystals as in Example I.

The extraction with chloroform as in this Example was more efficient. The pigment collected here was run on the silica gel column of Example I, yielding only two fractions, of which the blue was the more dominant.

EXAMPLE III

Morchella nov. ES-1 sp. (ATCC 20951) mycelia were grown and transferred into a shake flask as in Example I, and then pre-grown for 48 hours at 150 rpm at 28° C. This point was prior to the medium turning from yellow to blue in color. The mycelia were homogenized using a Tekmar Tissumizer TM homogenizer.

The fragmented mycelia were used as inoculum for a 15.0 L fermenter containing 10.0 L of the liquid medium listed in Example I which previously had been sterilized for 45 minutes at 121° C. The inoculum to the fermenter was 3.0% (v/v). Cultivation conditions were as follows:

| Temperature | 28° C. |
| --- | --- |
| Agitation speed | 400 rpm |
| Initial pH | 6.5 |
| Aeration rate | 1.0 vvm |

The fermentation was complete at the end of 96 hours (that is, the medium had turned dark blue). The mycelia were separated from the medium by screening through a synthetic fabric having pore diameters of 0.1 mm. The mycelia beads were dried via vacuum at 40° C. The dried mycelia were extracted with chloroform as described in Example II. The resulting pigment was concentrated by evaporation in a rotary evaporator at 35° C. until crystallization of the pigment occurred.

EXAMPLE IV

The Morchella nov. ES-1 sp. mutant fungus of this invention was compared with two mutant fungal strains described by Miles et al. (ATCC 12671 and 36481) and one wild strain (ATCC 58747). The two mutant strains of *Schizophyllum commune* had been deposited with ATCC by Miles and are described as being capable of producing indigo in submerged culture.

Mycelia of each strain were inoculated onto petri dishes containing the following agar medium: 1.0% glucose, 0.5% pepton,e 0.5% yeast extract, 0.5% malt extract and 1.5% agar. The dishes were incubated at 25° C. for 7 days and then visually compared. The results are shown in Table I.

TABLE I

| | Growth Pattern | Morphology |
| --- | --- | --- |
| S. commune (ATCC 58747) | Covered the dish | Hairy, white No agar color change |
| S. commune (ATCC 12671) | Spread as one colony over 30% of dish | Dusty, gray-white No agar color change |
| S. commune (ATCC 36481) | Multiple colonies | Fluffy, white; small beads No agar color change |
| ES-1 (ATCC 20951) | Multiple colonies | Fuzzy, white; Agar beneath colonies turning blue. |

It is apparent from the descriptions of Table I that the novel mutant strain of the present invention is not the same as the Miles *S. commune* fungal strains. Although similar in appearance to ATCC 36481, the ES-1 strain (ATCC 20951) was the only one to diffuse blue pigment into the agar medium. The ES-1 strain was also the only one in which blue granules were seen (via microscope) in the mycelia.

EXAMPLE V

The fungal strains of Example IV were compared in submerged fermentation. Each strain was transferred into three flasks containing the medium of Example I. The flasks were incubated at 28° C., and agitated at 150 rpm. The flasks were examined visually over 9 days for evidence of color change. After 3 days, flasks containing the ES-1 strain had turned dark blue. After 8 days, the flasks containing ATCC 12671 had turned slightly green. The color of the remaining flasks did not change over the 9 day period, even though there was considerable fungal growth.

EXAMPLE VI

Morchella nov. ES-1 sp. (ATCC 20951) mycelia were grown and cultivated by submerged fermentation as in Example I. Measurements wer emade at 120, 168 and 216 hours, with the results indicated in Table II.

TABLE II

| Time | pH | Glucose | Dry Weight of Mycelia | Indigo (mg/L) In Medium | Indigo (mg/L) In Mycelium |
| --- | --- | --- | --- | --- | --- |
| 0 | 6.1 | 30 gm/L | 0.0 gm/L | 0.0 | 0.0 |
| 120 | 5.0 | 0.35 gm/L | 2.97 gm/L | 2.4 | 4.9 |
| 168 | 5.4 | 0.29 gm/L | 3.80 gm/L | 12.7 | 13.9 |
| 216 | 5.6 | 0.22 gm/L | 3.52 gm/L | 8.5 | 21.7 |

EXAMPLE VII

Morchella nov. ES-1 sp. (ATCC 20951) were grown and cultivated by submerged fermentation as in Example I with the following changes: temperature=30° C. and glucose concentration fo medium=60 gm/L. Measurements were made at 120, 168 and 216 hours, with the results indicated in Table III.

TABLE III

| Time | pH | Glucose | Culture Dry Wt. | Indigo (mg/L) In Medium | Indigo (mg/L) In Mycelium |
| --- | --- | --- | --- | --- | --- |
| 0 | 6.1 | 60 gm/L | 0 | 0 | 0 |
| 120 | 4.7 | 1.3 gm/L | 5.89 | 1.2 | 2.4 |
| 168 | 5.0 | 0.4 gm/L | 4.81 | 8.5 | 14.2 |
| 216 | 5.3 | 0.3 gm/L | 3.38 | 11.6 | 13.1 |

The principles, preferred embodiments and modes of operation of the present invention have been described in the foregoing specification. The invention which is intended to be protected herein, however, is not to be construed as limited to the particular forms disclosed, since these are to be regarded as illustrative, rather than restrictive. Variations and changes may be made by those skilled in the art without departing from the spirit of the invention.

We claim:

1. A biologically pure culture of *Morchella rotunda* nov. ES-1 sp. which has the characteristics identified as ATCC 20951 and has the ability to produce the blue pigment indigo by submerged fermentation in a nutrient culture medium comprising a carbon substrate and a nitrogen substrate.

2. The culture of claim 1 which has the ability to efficiently produce indigo in a medium comprising about 2.0 to about 5.0% of a carbon substrate and about 0.5 to about 5.0% of a nitrogen substrate.

3. The culture of claim 1 which has the ability to efficiently produce indigo in a medium which also comprises inorganic elements.

4. The culture of claim 1 which has the ability to efficiently produce indigo in a medium which also comprises vitamins.

5. The culture of claim 1 which also has the ability to produce a red/purple pigment by said submerged fermentation.

* * * * *